United States Patent
Place

(10) Patent No.: US 6,180,682 B1
(45) Date of Patent: Jan. 30, 2001

(54) BUCCAL DRUG DELIVERY SYSTEM FOR USE IN MALE CONTRACEPTION

(75) Inventor: Virgil A. Place, P.O. Box 44555 - 10 Ala Kahua, Kawaihae, HI (US) 96743

(73) Assignee: Virgil A. Place, Kawaihae, HI (US)

(*) Notice: Under 35 U.S.C. 154(b), the term of this patent shall be extended for 0 days.

This patent is subject to a terminal disclaimer.

(21) Appl. No.: 09/237,455

(22) Filed: Jan. 26, 1999

(51) Int. Cl.$^7$ .................................................. A61K 9/20
(52) U.S. Cl. ........................ 514/841; 424/435; 424/464
(58) Field of Search .................................. 424/435

(56) References Cited

U.S. PATENT DOCUMENTS

| | | | |
|---|---|---|---|
| 4,346,709 | * 8/1982 | Schmitt | 128/260 |
| 4,704,285 | 11/1987 | Alderman | 424/468 |
| 4,755,386 | 7/1988 | Hsiao et al. | 424/435 |
| 4,764,378 | 8/1988 | Keith et al. | 424/435 |
| 4,877,774 | 10/1989 | Pitha et al. | 514/26 |
| 5,135,752 | 8/1992 | Snipes et al. | 424/435 |
| 5,346,701 | 9/1994 | Heiber et al. | 424/435 |
| 5,516,523 | 5/1996 | Heiber et al. | 424/435 |

OTHER PUBLICATIONS

Bebb et al. (1996), "Combined Administration of Levonorgestrel and Testosterone Induces More Rapid and Effective Suppression of Spermatogenesis than Testosterone Alone: A Promising Male Contraceptive Approach," *J. Clin. Endocr. Metab.* 81: 757–762.

Bhasin et al. (1997), "Emerging Issues in Androgen Replacement Therapy," *J. Clin.. Endocr. Metab.* 82:3–8.

Cummings et al. (1994), "Prospects for New Hormonal Male Contraceptives," *Clin. Androl.* 23:893–992.

Meriggiola et al. (1996), "A Combined Regimen of Cyproterone Acetate and Testosterone Enanthate as a Potentially Highly Effective Male Contraceptive," *J. Clin. Endocr. Metab.* 81:3018–3023.

Meriggiola et al. (1997), "Progestin–Androgen Combination Regimens for Male Contraception," *J. Androl.* 18:240–244.

Pavlou et al. (1991), "Combined Administration of a Gonadotropin–Releasing Hormone Antagonist and Testosterone in Men Induces Reversible Azoospermia without Loss of Libido," *J. Clin. Endocr. Metab.* 73:1360–1369.

Tom et al. (1992), "Induction of Azoospermia in Normal Men with Combined Nal–Glu Gonadotropin–Releasing Hormone Antagonist and Testosterone Enanthate," *J. Clin. Endocr. Metab.* 75:476–483.

* cited by examiner

*Primary Examiner*—Shelley A. Dodson
*Assistant Examiner*—Konata M. George
(74) *Attorney, Agent, or Firm*—Dianne E. Reed; Louis L. Wu; Reed & Associates

(57) ABSTRACT

A buccal dosage unit is provided for administering a contraceptive composition to fertile mammalian males. The buccal dosage unit comprises a an androgenic agent and a progestin in a polymeric carrier that bioerodes and provides for delivery of the active agents throughout a predetermined drug delivery period that is preferably in the range of approximately 8 to 24 hours.

40 Claims, 2 Drawing Sheets

BUCCAL DRUG DELIVERY SYSTEM FOR USE IN MALE CONTRACEPTION

TECHNICAL FIELD

This invention relates generally to pharmaceutical compositions and methods for administering pharmacologically active agents. More particularly, the invention relates to buccal drug delivery, and to a buccal dosage unit and method for administering a contraceptive composition to a mammalian male.

BACKGROUND

To date, there are no commercially available oral contraceptive methods for males which are safe, reliable, and effective. Currently available male contraceptive methods suffer from the disadvantages of being unreliable, cumbersome, or, in the case of vasectomy, generally irreversible. In spite of these drawbacks, approximately 35% of contraception worldwide involves male practices. *Popul. Rep.* (1986)14: J889.

It has been proposed that spermatogenesis is driven by gonadotropins. Gonadotropin releasing hormone (GnRH), a decapeptide released in bi-hourly pulses from the hypothalamus, pituitary secretion of fofficle-stimulating hormone (FSH) and luteinizing hormone (LH) regulate the functioning of the gonads to produce testosterone in the testes and the production and maturation of gametes. Within the testis, FSH binds to specific receptors on Sertoli cells, and LH stimulates Leydig cells. In addition, LH stimulates cells to produce testosterone, which interacts with intracellular androgen receptors in testicular Sertoli and peritubular cells. Spermatogenesis is thus thought to be driven by both FSH and testosterone. Accordingly, most hormonal approaches to male contraception have focused on inhibition of G gonadotropins, or both.

Exogenously administered androgens inhibit gonadotropin secretion, consequently inhibiting spennatogenesis, and have been studied as potential contraceptive agents in men. Cummings et al. (1994) *Clin. Androl.* 23:893–992. An intramuscular (IM) injection of 200 mg per week of testosterone enanthate results in azoospermia in 50% to 70% of Caucasian men and 95% of Asian men after approximately 4 months. Side effects included oily skin, acne, irritation of the injection site, an increase in aggressiveness, a decrease of the high-density lipoprotein (HDL)-cholesterol and possible adverse effects on the prostate gland.

The effect of lower doses of testosterone enanthate in combination with prosgestogenic agents has also been studied and has been reported to produce azoospermia comparable to those obtained with high doses of testosterone enanthate alone. An IM injection of 100 mg per week of testosterone enanthate in combination with 500 µg per day of levonorgestrel administered orally resulted in about 67% of the males achieving azoospermia in about 10 weeks. The side effects included a slight gain in weight and a significant decrease in the serum HDL-cholesterol. Bebb et al. (1996) *J. Clin. Endocr. Metab.* 81:757–762.

Co-administration of testosterone enanthate (100 mg/week, IM injection) with the synthetic steroid cyproterone acetate (100 mg/day or 50 mg per day) has been evaluated and was found to result in azoospernia within 7 to 8 weeks. However, the side effects included a slight decrease in body weight and a significant decrease in testis size during treatment. Meriggiola et al. (1996) *J. Clin. Endocr. Metab.* 81:3018–3023; Meriggiola et al. (1997) *J. Androl.* 18:240–244.

In another study, testosterone enanthate (25 mg/week, IM injection) was co-administered with a GnRH antagonist Nal-Glu (10 mg/day, subcutaneous injection). This combination resulted in azoospermia in approximately 75% of the men tested. However, the major side effect was an increase in the concentration of HDL-cholesterol. Pavlou et al. (1991) *J. Clin. Endocr. Metab.* 73:1360–1369; Tom et al. (I992) *J. Clin. Endocr. Metab.* 75:476–483.

The methods of effecting male contraception using testosterone enanthate currently being studied require intramuscular or a subcutaneous injection that can be painful. In addition, self-administration of an injectable composition typically suffers from low user acceptance.

Attempts at alternative routes of administration have not been successful for a number of reasons. Testosterone, for example, is well absorbed after oral administration but is quickly metabolized during passage through the liver and intestine. Therefore, it is not possible to achieve effective blood levels of testosterone via oral administration. 17α-alkylated derivatives of testosterone can be administered orally and are resistant to hepatic metabolism, but are not recommended for clinical use because of their potential hepatoxicity. Bhasin et al. (1997) *J. Clin. Endocr. Metab.* 82:3–8. Delivery of testosterone through the skin has been achieved using conventional transdenmal patches. However, transdermal administration of steroids requires a permeation enhancer, which can result in skin irritation and sensitization.

Drug therapy involving buccal administration of steroid hormones has been described. For example, U.S. Pat. No. 4,755,386 to Hsiao et al. generally describes the buccal administration of various medicaments, including estrogens, progestins and androgens; however, male contraceptive compositions are not contemplated. U.S. Pat. No. 4,764,378 to Keith et al. describes rapidly disintegrating dosage forms utilizing a combination of high and low molecular weight polyethylene glycols; the dosage forms, which are preferably 50 mg to 100 mg tablets, may be administered orally or through the buccal mucosa. Similarly, U.S. Pat. No. 5,135,752 to Snipes et al. describes buccal delivery systems containing polyethylene glycols of varying molecular weights for the delivery of methyl testosterone or estadiol. U.S. Pat. No. 4,877,774 to Pitha et al. describes crystalline complexes of steroid hormones and gamma-cydodextrin for administration of steroids through mucosal tissue.

The present male contraceptive compositions and methods are, however, new and completely unsuggested by the art. Applicants' contraceptive compositions are in the form of a compact drug dosage unit to be applied to the buccal mucosa, wherein the dosage unit comprises an androgenic agent and a progestin in a bioerodible polymeric carrier that facilitates adhesion to the buccal mucosa. The present buccal dosage units provide for a highly effective method of male contraception, and overcome a number of the disadvantages associated with prior male contraceptive compositions and methods. In particular, the present buccal dosage units, in contrast to the prior art, are simple in design and easily manufactured, are pharmacologically reliable, and do not result in the side effects associated with intramuscular injection, transdermal drug delivery or other modes of administration.

SUMMARY OF THE INVENTION

Accordingly, it is a primary object of the invention to address the aforementioned need in the art by providing a drug dosage unit for buccally administering to a male individual a pharmaceutical composition comprising an androgenic agent and a progestin.

It is another object of the invention to provide a method for effecting contraception in a male individual by buccally administering a contraceptive composition using the aforementioned drug dosage unit.

Additional objects, advantages and novel features of the invention will be set forth in part in the description which follows, and in part will become apparent to those skilled in the art upon examination of the following, or may be learned by practice of the invention.

Accordingly, in a first embodiment, then, a pharmaceutical composition is provided in the form of a simple, compact buccal dosage unit comprising therapeutically effective amounts of an androgenic agent and a progestin in a bioerodible polymeric carrier, wherein the carrier is such that it enables the dosage unit to adhere to the buccal mucosa. Following application to the buccal mucosa, gradual and complete erosion of the unit occurs over a predetermined time period, thus providing drug delivery throughout that time period. In a preferred embodiment, the dosage unit contains only the active agents to be administered and the polymeric carrier. However, other components, particularly a lubricant, may be incorporated to facilitate manufacture of the unit or if otherwise found to be necessary or desirable. The buccal dosage units are typically far smaller than conventional buccal delivery systems—the present tablets are on the order of 5–20 mg, typically 10–15 mg—and do not require a plurality of excipients, disintegrants, adhesives, or the like, nor are fragrances or permeation enhancers necessary. Accordingly, the novel dosage units are more comfortable than conventional systems because of their compact size. The novel units are also highly effective in providing effective contraceptive levels of steroidal agents. While the dosage units are designed to erode and thus deliver the active agents over a predetermined time period that is generally in the range of about 8 hours to about 24 hours, 12-hour dosage units are preferred, such that the individual receiving drug therapy can conveniently use two dosage units in a 12-hour period, enabling two "breaks" for dental hygiene or the like during the day. In this regard, the dosage units can be applied to an area of a subject's buccal mucosa such that the subject can eat and/or drink with the unit in place.

In another embodiment of the invention, a method is provided for effecting contraception in a mammalian male, comprising buccally administering the aforementioned contraceptive composition comprising an androgenic agent and a progestin. The composition is administered through the buccal mucosa by affixing a dosage unit as provided herein to the buccal mucosa and allowing the dosage unit to remain in place until erosion is complete.

In an additional embodiment of the invention, a kit is provided to assist an individual in buccal drug adminstration. Generally, the kit includes the following components: a buccal dosage unit comprising a contraceptive composition and a bioerodible polymeric carrier; a container housing the dosage unit prior to use; and written instructions for carying out administration of the composition. These objects, embodiments and features of the invention will become apparent to those skilled in the art upon reading the following disclosures and description of the invention.

DETAILED DESCRIPTION OF THE INVENTION

Figure 1:
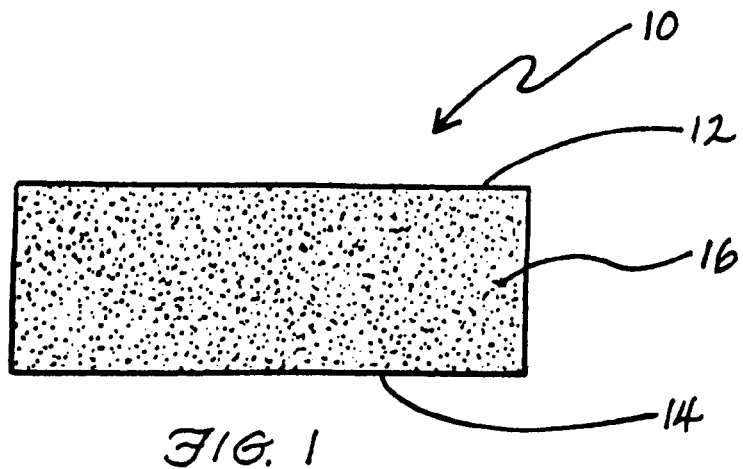
FIG. 1 schematically illustrates a preferred embodiment of a buccal dosage unit according to the invention.

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "an androgenic agent" includes a mixture of two or more androgenic agents, reference to "a progestin" includes a mixture of two or more progestins, reference to "a polymeric carrier" includes mixtures of two or more suitable polymeric carriers, and the like.

In describing and claiming the present invention, the following terminology will be used in accordance with the definitions set out below.

The terms "drug" or "pharmacologically active agent" or "active agent" as used herein refer to a compound or composition of matter which, when administered to an organism (human or animal) induces a desired phamacologic and/or physiologic effect by local and/or systemic action. The active agents herein are steroid hormones, including androgenic agents, e.g., testosterone and derivatives, analogs, esters and salts thereof, and progestins, e.g. progesterone, cyproterone acetate, norethindrone, norethindrone acetate or levonorgestrel.

By "buccal" drug delivery is meant delivery of a drug by passage of a drug through the buccal mucosa into the bloodstream. Preferably, buccal drug delivery is effected herein by placing the buccal dosage unit on the upper gum or opposing inner lip area of the individual undergoing drug therapy.

"Penetration enhancement" or "permeation enhancement" as used herein relates to an increase in the permeability of the buccal mucosal tissue to a pharmacologically active agent, i.e., so that the rate at which the drug permeates through the mucosal tissue is increased.

"Excipients" or "vehicles" as used herein refer to any excipients or vehicles suitable for buccal drug administration, and include any such materials known in the art, e.g., any liquid, gel, solvent, liquid diluent, solubilizer, or the like, which is nontoxic and which does not interact with other components of the composition in a deleterious manner.

By an "effective" amount of a pharmacologically active agent or pharmaceutical composition is meant a nontoxic but sufficient amount of the agent or composition to provide the desired effect. Thus, in the context of the present invention, an "effective" amount of a pharmacologically active agent or pharmaceutical composition is an amount sufficient to effect contraception.

"Compact" as used herein refers to a buccal dosage unit that is preferably no larger than about 5 mm in diameter and 2 mm in height, so that the unit occupies at most about 40 mm³, typically weighs less than about 40 mg (preferably 5 to 20 mg, more preferably 10 to 15 mg), and has a contact surface area of no more than approximately 20 mm³.

The terms "erodible" and "bioerodible" as used herein refer to a compound or composition that hydrolyzes upon contact with the buccal mucosa.

In one embodiment, then, a pharmaceutical composition is provided in the form of a buccal dosage unit for the administration of a combination of steroidal agents, i.e., an androgenic agent and a progestin. The dosage unit comprises (a) effective amount of an androgenic agent and a progestin, and (b) a bioerodible polymeric carrier as will be described in detail below. The dosage unit is fabricated so as to erode gradually over a predetermined time period, wherein drug delivery is provided essentially throughout. The time period is typically in the range of 8 hours to 24 hours; that is, for an 8-hour unit, erosion will occur throughout an 8-hour period and be substantially complete at the 8-hour point, while for a 24-hour unit, erosion will occur throughout a 24-hour period and be substantially complete at the 24-hour point. The buccal dosage unit may further comprise a lubricant to facilitate manufacture, e.g., magnesium stearate or the like. Additional components that may be included in the buccal dosage unit, but are neither required nor preferred, are flavorings, permeation enhancers, diluents, binders, and the like. As a buccal drug delivery system, the novel dosage unit avoids the disadvantages encountered with oral drug administration, e.g., degradation of active agents by fluids present in the gastrointestinal tract and/or first-pass inactivation in the liver. In addition, because of its compact size, the unit is not associated with the discomfort encountered with larger, conventional buccal drug delivery systems. Also, the units are convenient in that the wearer need change the unit only once or twice daily, i.e., with 24-hour or 12-hour systems, respectively; a 12-hour unit to be applied once in the morning and once in the evening is optimal. Finally, because of the compositional simplicity of the unit—in a preferred embodiment, the unit contains only the active agents and the polymeric carrier—manufacture of the dosage form is straightforward and economical.

Suitable androgic agents that may be used in the formulations of the present invention include, but are not limited to: the naturally occurring androgens and derivatives thereof including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone and testosterone esters, such as testosterone enanthate, testosterone propionate and testosterone cypionate, are particularly preferred androgenic agents for use in conjunction with the present invention. The aforementioned testosterone esters are commercially available or may be readily prepared using techniques known to those skilled in the art or described in the pertinent literature. (Generally, the 17-hydroxyl group of the testosterone molecule is caused to react with a suitable organic acid under esterifying conditions, such conditions typically involving the use of a strong acid such as sulfuric acid, hydrochloric acid, or the like, and a temperature sufficient to allow the reaction to proceed at reflux.)

Suitable progestins for use in the buccal drug delivery units of the invention include, but are not limited to, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Progesterone, cyproterone acetate, norethindrone, norethindrone acetate and levonorgestrel are preferred progestins.

The aforementioned steroidal agents are selected from the group consisting of naturally occurring steroids, synthetic steroids, and derivatives thereof The active agents may be incorporated into the present dosage units and thus administered in the form of a pharmaceutically acceptable derivative, analog, ester or salt, or the agents may be modified by appending one or more appropriate functionalities to enhance selected biological properties such as penetration through the mucosal tissue. In general, with regard to androgenic agents, esters are preferred relative to salts or other derivatives. Preparation of esters involves functionalization of hydroxyl and/or carboxyl groups that may be present, as will be appreciated by those skilled in the arts of pharmaceutical chemistry and drug delivery. Esters can be reconverted to the free acids, if desired, by using conventional hydrogenolysis or hydrolysis procedures.

To administer any one of the active agents in salt form, suitable pharmaceutically acceptable salts can be prepared using standard procedures known to those skilled in the art of synthetic organic chemistry and described, for example, by J. March, *Advaced Organic Chemistry: Reactions, Mechanisms and Structure*, 4th Ed. (New York: Wiley-Interscience, 1992). Acid addition salts are prepared from an active agent in the free base form (e.g., compounds having a neutral —NH₂ group) using conventional means, involving reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuic acid, nitric acid, phosphoric acid, and the like. An acid addition salt may be reconverted to the free base by treatment with a suitable base. Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

For those active agents that are chiral in nature and can thus be in enantiomerically pure form or in a racemic mixture, the drug may be incorporated into the present dosage units either as the racemate or in enantiomerically pure form.

The quantity of active agents in the buccal dosage unit will depend on the potency of each agent and the intended dosage. Suitable doses of androgenic agents and progestins agents will be known to those skilled in the art, or may be deduced from the literature in combination with the teaching of the present disclosure. The active agents will generally represent on the order of 40 wt. % to about 80 wt. % of the dosage unit, preferably on the order of 50 wt. % to about 75 wt. %. The remainder of the composition is comprised of a carrier as will be described in detail below.

Ideally, the carrier comprises a polymer having sufficient tack to ensure that the dosage unit adheres to the buccal mucosa for the necessary time period, i.e., the time period during which the combination of steroidal agents is to be delivered to the buccal mucosa. Additionally, the polymeric carrier is gradually "bioerodible," i.e., the polymer hydrolyzes at a predetermined rate upon contact with moisture. The polymer is preferably sticky when moist, but not when dry, for convenience in handling. Generally, it is preferred that the weight average molecular weight ($M_w$) of the polymer be in the range of approximately 4,000 to 1,000,000, more preferably in the range of approximately 100,000 to 1,000,000. One of skill in the art will appreciate that the higher the molecular weight of the polymer, the slower the erosion time.

Any polymeric carriers can be used that are pharmaceutically acceptable, provide both a suitable degree of adhesion and the desired drug release profile, and are compatible with the agents to be administered and any other components that maybe present in the buccal dosage unit. Generally, the polymeric carriers comprise hydrophilic (water-soluble and water-swellable) polymers that adhere to the wet surface of the buccal mucosa. Examples of polymeric carriers useful herein include acrylic acid polymers and copolymers, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, sodium carboxymethyl cellulose, methyl cellulose, ethyl cellulose, cellulose acetate phthalate, cellulose acetate butyrate, and the like. The carrier may also comprise two or more suitable polymers in combination, for example, a caibomer combined in an approximately 1:5 to 5:1 ratio, by weight, with a polyethylene oxide.

It is preferred that the present dosage unit contain only the active agents and the polymeric carrier. However, it may be desirable in some cases to include one or more additional components. For example, a lubricant may be included to facilitate the process of manufacturing the dosage units; lubricants may also optimize erosion rate and drug flux. If a lubricant is present, it will represent on the order of 0.01 wt. % to about 2 wt. %, preferably about 0.01 wt. % to 0.5 wt, %, of the dosage unit. Suitable lubricants include, but are not limited to, magnesium stearate, calcium stearate, stearic acid, sodium stearygfuarate, talc, hydrogenated vegetable oils and polyethylene glycol. As will be appreciated by those silled in the art, however, modulating the particle size of the components in the dosage unit and/or the density of the unit can provide a similar effect—i.e., improved manufacturability and optinization of erosion rate and drug flux—without addition of a lubricant.

Other components may also be incorporated into the buccal dosage unit; however, it must be emphasized that such components are neither required nor preferred. Such additional optional components include, for example, one or more disintegrants, diluents, binders, enhancers, or the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallizll sucrose and dextrin such as Di-Pak®, which may be obtained from Amstar), lactone, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the androgenic agent passes through the buccal mucosa. Examples of permeation enhancers include, but are not limited to, dimethylsulfoxide ("DMSO"), dimethyl formamide ("DMF"), N,N-dimethylacetamide ("DMA"), decylmethylsuifoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), lower alkanols (e.g., ethanol), SEPA® (available from Macrochem Co., Lexington, Mass.), cholic acid, taurocholic acid, bile salt type enhancers, and suifactants such as Tergitol®, Nonoxynol-9® and TWEEN-80®. Preferred dosage units of the invention, however, do not contain permeation enhancers.

Flavorings are not typically needed in the present drug dosage units, as the active agents do not, in general, have any taste. If for some reason a flavoring is desired, any suitable flavoring may be used, e.g., mannitol, lactose or artificial sweeteners such as aspartame. Coloring agents may be added, although again, such agents are not required. Examples of coloring agents include any of the water soluble FD&C dyes, mixtures of the same, or their corresponding lakes.

In addition, if desired, the present dosage units may be formulated with one or more preservatives or bacteriostatic agents, e.g., methyl hydroxybenzoate, propyl hydroxybenzoate, chlorocresol, benzalkonium chloride, or the like.

Additionally, one or more additional types of drugs, i.e., pharmacologically active agents other than androgenic agents and progestins, may be incorporated into the present dosage units. For example, other types of steroid drugs may be administered along with the androgenic agent and the progestin. Such steroid drugs are selected from the group consisting of naturally occurring steroids, synthetic steroids, derivatives thereof pharmaceutically acceptable salts, esters and inclusion complexes of any of the foregoing, and combinations thereof.

In another embodiment of the invention, a method is provided for administering a contraceptive composition to a mammalian male using the buccal dosage units described hereinabove, wherein the contraceptive composition comprises an androgenic agent and a progestin. The method generally comprises buccally administering the contraceptive composition by affixing the dosage unit of the invention to the buccal mucosa of the individual and allowing the dosage unit to remain in place until erosion thereof—and thus drug delivery—is complete.

The buccal dosage units may be in the form of tablets made by either conventional compression or molding methods. See, e.g., Remington's Pharmaceutical Sciences, 18$^{th}$ edition, (Easton, Pa.: Mack Publishing Co., 1990). Preferably, the dosage units are prepared by mixing the components together and compressing the mixture into tablet form. As will be appreciated by those skilled in the art, the erosion rate of the dosage unit, and thus the rate of drug delivery, is controlled by three factors: the pressure used to make a tablet, and thus the tablets' density; the carrier selected, as alluded to above; and the carrier-to-drug ratio. Pressure, carrier and carrier-to-drug ratio may thus be varied to obtain shorter acting or longer-lived dosage units.

Figure 2:
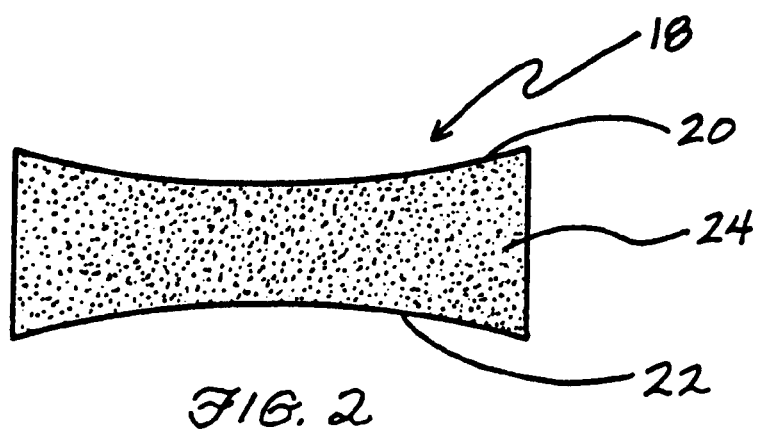
FIG. 2 schematically illustrates an alternative embodiment of a buccal dosage unit according to the invention.
Figure 3:
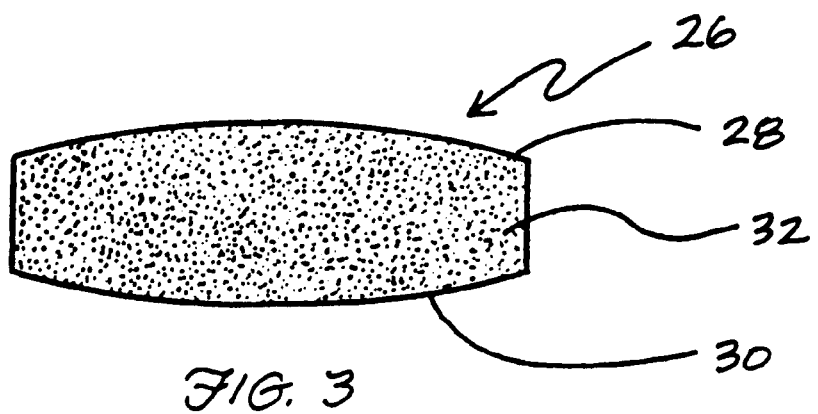
FIG. 3 schematically illustrates a second alternative embodiment of a buccal dosage unit according to the invention.

The dosage units herein may have any of the conventional shapes, for example, lozenges, disks, wafers, tablets or the like. One possible configuration is a conventional tablet shape as shown in FIG. 1, with the dosage unit indicated generally at 10, the pharmaceutical composition per se shown at 12, and the dosage unit's two parallel substantially planar surfaces shown at 14 and 16; either surface can be used to affix the unit to the buccal mucosa. A more preferred configuration is shown in FIG. 2, wherein the dosage unit is shown generally at 18 with the composition at 20, and the two opposing concave surfaces at 22 and 24; the opposing concave surfaces allow for a suction effect and improve adhesion of the unit to the mucosal tissue. A less preferred configuration is shown in FIG. 3, wherein the dosage unit shown generally at 26, containing pharmaceutical composition 28, has opposing convex surfaces 30 and 32.

The dosage unit should have dimensions which fit conveniently into the buccal cavity, and, as emphasized elsewhere herein, is preferably quite compact. By way of example, suitable dimensions for the dosage unit are 2 mm to about 5 mm in diameter, preferably not exceeding about 5 mm in diameter, and about 0.3 to about 2 mm in thickness, preferably about 0.5 to 1.5 mm in thickness, most preferably about 0.5 to 1.1 mm in thickness. The total weight of the dosage unit may be from about 5 mg to about 20 mg, preferably 10 mg to about 15 mg.

The buccal formulations of the present invention may also be generated by a molding process. Preferably, the final composition should have a melting point which is high enough to prevent fusion of packaged dosage units during shipping and storage, yet low enough to permit mixing of pharmaceutical ingredients without significant decomposition of the active agents when being incorporated into the molten carrier.

Figure 4:
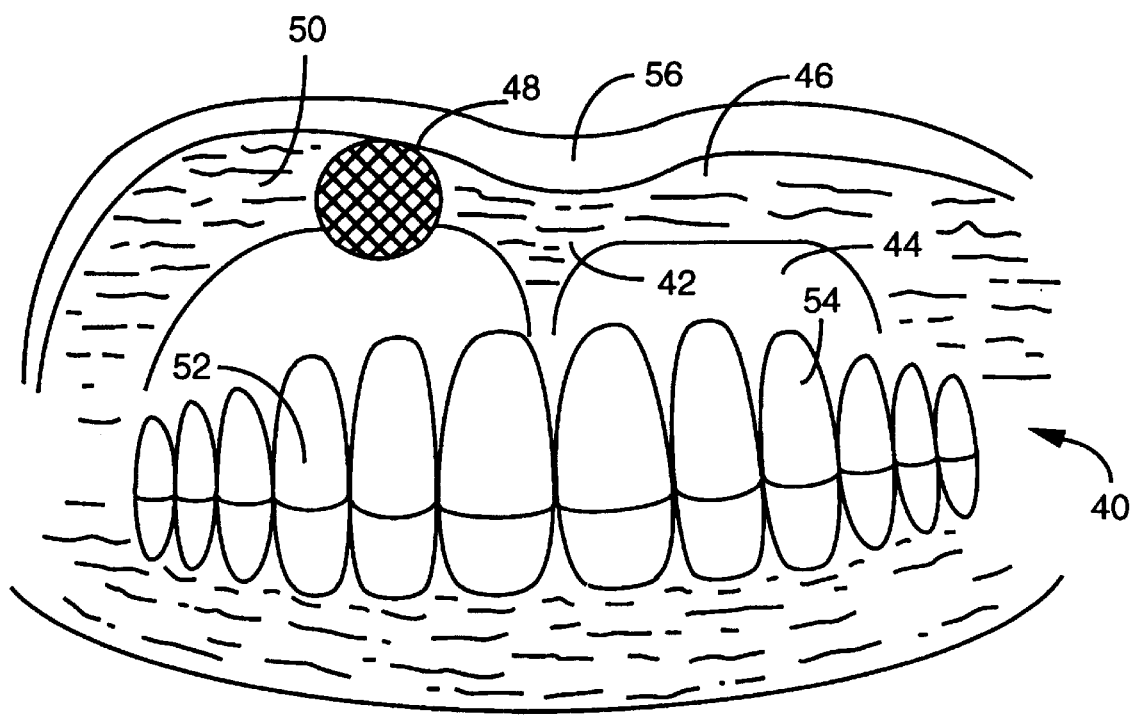
FIG. 4 illustrates the placement of the buccal dosage unit in the preferred location in the oral cavity.

The preferred position for placement of the dosage unit in the buccal cavity, as illustrated in FIG. 4, is in the oral vestibule, generally indicated at 40, on the anterior surface 42 of the gum, between the marginal gingiva 44 and the reflexion of the mucosa from the lips to the gums 46, i.e., the dosage unit 48 is preferably attached to the alveolar mucosa 50, between the two bicuspids 52 and 54 and slightly to one side of the medial plane defined thereby. Such positioning places the dosage unit in contact with the mucosa on the internal surface of the lips 56 as well as the alveolar mucosa 50. Such placement provides advantages for optimal drug delivery. For example, when so positioned, the dosage unit is out of the salivary flow path and is less likely to detach from the gum when the subject eats or drinks. Being out of the salivary flow path allows optimal direct transmucosal delivery of the active agents, any saliva that contacts the unit resulting not in dissolution of the active agents but, primarily, in softening the carrier. In addition, positioning the dosage unit as described inimzes mobility of the active agents in the mouth. Furthermore, the dosage unit will be in contact with both the alveolar mucosa and the internal mucosal surface of the lips, resulting in hydrolysis of the carrier, and thus absorption of the active agents through mucosa, on both sides of the tablet.

The invention also encompasses a kit for patients to carry out the aforementioned methods. The kit contains the contraceptive composition to be administered in a buccal dosage unit (e.g., as shown in FIGS. 1, 2 or 3), a sealed container housing the dosage unit prior to use, and written instructions for drug administration.

It is to be understood. that while the invention has been described in conjunction with the preferred specific embodiments thereof that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Buccal dosage units weighing approximately 10 mg to 15 mg each and containing testosterone and norethindrone as the active agents are prepared using a tablet direct press, as follows.

| "T1" Tablet Composition | |
|---|---|
| % BY WEIGHT | COMPONENT |
| 50% | Testosterone (USP, micronized, Pharmacia Upjohn) |
| 35% | Norethindrone (USP, micronized Pharmacia Upjohn) |
| 14.8% | Polyethylene oxide (Polyox ® WSR-303, Union Carbide) |
| 0.2% | Magnesium Stearate |
| 100% | |

All components (i.e., testosterone, norethindrone, polyethylene oxide and magnesium stearate, as set forth in the above table) are thoroughly mixed prior to tablet formation using aqueous fluid bed granulation to provide a homogeneous mixture of active agents and excipients. The individual dosage units are then made by applying approximately 10 to 15 mg of the mixture into the punch die of a tablet press, and compressing the mixed components using a pressure in the range of approximately 500 to 2000 psi. Tablets having a diameter of approximately 4 mm and a height of 1 mm are prepared. The tablet is removed from the punch die and the weight and dimensions of the tablet are measured.

EXAMPLE 2

Buccal dosage units containing a mixture of polymeric carriers and having the following composition were prepared as described in Example 1.

"T2" Tablet Composition

| % BY WEIGHT | COMPONENT |
|---|---|
| 50% | Testosterone (USP, micronized, Pharmacia Upjohn) |
| 35% | Norethindrone (USP, micronized, Pharmacia Upjohn) |
| 10% | Polyethylene oxide (Polyox ® WSR-303, Union Carbide) |
| 4.8% | Carbomer (Carbopol ®, NF) |
| 0.2% | Magnesium Stearate |
| 100% | |

EXAMPLE 3

IN VIVO EVALUATION

A contraceptive composition is administered to a male individual using a buccal dosage unit described in Example 1 (T1). Plasma samples are collected and analyzed for total testosterone, free testosterone, dihydrotestosterone, norethindrone and estradiol levels prior to treatment and at four-hour intervals after the start of treatment. The method is repeated using the same individual and the buccal dosage unit prepared as in Example 2 (T2). Finally, the method is repeated using the same individual and a placebo. The results suggest that the increase in testosterone and norethindrone levels following buccal administration is comparable to that obtained with transdermal testosterone administration, i.e., therapeutic levels of testosterone and norethindrone can be obtained.

What is claimed is:

1. A buccal dosage unit for use in male contraception, comprising a compressed tablet of a polymeric carrier which adheres to the oral mucosa and erodes upon sustained contact therewith over a period of approximately eight to twenty-four hours, and, incorporated in the polymeric carrier, a contraceptive composition comprising an androgenic agent and a progestin, wherein the weight of the tablet is in the range of approximately 5 mg to 20 mg.

2. The dosage unit of claim 1, wherein the androgenic agent is selected from the group consisting of androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepi-androsterone, sodium dehydroepiandrosterone sulfate, dromostanolone, dromostanolone propionate, ethylestrenol, fluoxymesterone, methyl testosterone, nandrolone phenpropionate, nandrolone decanoate, nandrolone furylpropionate, nandrolone cyclohexanepropionate, nandrolone benzoate, nandrolone cyclohexanecarboxylate, oxandrolone, oxymetholone, stanozolol, testosterone, 4-dihydrotestosterone, 5α-dihydrotestosterone, testolactone, pharmaceutically acceptable esters and salts thereof, and combinations of any of the foregoing.

3. The dosage unit of claim 2, wherein the androgenic agent is testosterone or a pharmaceutically acceptable ester thereof.

4. The dosage unit of claim 3, wherein the androgenic agent is a testosterone ester.

5. The dosage unit of claim 4, wherein the testosterone ester is selected from the group consisting of testosterone enanthate, propionate, cypionate, phenylacetate, acetate, buciclate, heptanoate, decanoate, undecanoate, caprate and isocaprate.

6. The dosage unit of claim 5, wherein the testosterone ester is selected from the group consisting of testosterone enanthate, propionate and cypionate.

7. The dosage unit of claim 3, wherein the androgenic agent is testosterone.

8. The dosage unit of claim 1, wherein the progestin is selected from the group consisting of acetoxypregnenolone, allylestrenol, anagestone acetate, chlormadinone acetate, cyproterone, cyproterone acetate, desogestrel, dihydrogesterone, dimethisterone, ethisterone, ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, and combinations thereof.

9. The dosage unit of claim 8, wherein the progestin is selected from the group consisting of progesterone, cyproterone acetate, norethindrone, norethindrone acetate and levonorgestrel.

10. The dosage unit of claim 1, wherein the polymeric carrier is selected from the group consisting of carbomers, hydrolyzed polyvinylalcohol, polyethylene oxide, polyacrylates, hydroxypropyl methylcellulose, hydroxypropyl cellulose, and combinations thereof.

11. The dosage unit of claim 10, wherein the carrier is polyethylene oxide or a carbomer.

12. The dosage unit of claim 11, weighing in the of approximately 10 mg to 15 mg.

13. The dosage unit of claim 1, wherein the androgenic agent and the progestin together represent approximately 40 wt. % to 85 wt. % of the unit.

14. The dosage unit of claim 13, wherein the androgenic agent and the progestin together represent approximately 50 wt. % to 85 wt. % of the unit.

15. A buccal dosage unit for use in male contraception, comprising a compressed tablet of a polymeric carrier which adheres to the oral mucosa and erodes upon sustained contact therewith over a period of approximately eight to twenty-four hours, and, incorporated in the polymeric carrier, a contraceptive composition comprising an androgenic agent selected from the group consisting of testosterone and testosterone enanthate and a progestin selected from the group consisting of norethindrone and norethindrone acetate, and wherein the weight of the tablet is in the range of approximately 5 mg to 20 mg.

16. A method for effecting contraception in a mammalian male individual, comprising buccally administering to the individual a pharmaceutical composition comprising an androgenic agent and a progestin using the buccal dosage unit of claim 1.

17. The method of claim 16, wherein the androgenic agent is selected from the group consisting of androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17- benzoate, androstenedione, dehydroepiandrosterone, sodium dehydroepiandrosterone sulfate, dromostanolone, dromostanolone propionate, ethylestrenol, fluoxymesterone, methyl testosterone, nandrolone phenpropionate, nandrolone decanoate, nandrolone furylpropionate, nandrolone cyclohexane-propionate, nandrolone benzoate, nandrolone cyclohexanecarboxylate, oxandrolone, oxymetholone, stanozolol, testosterone, 4-dihydrotestosterone, 5α-dihydrotestosterone, testolactone, pharmaceutically acceptable esters and salts thereof, and combinations of any of the foregoing.

18. The method of claim 17, wherein the androgenic agent is testosterone or a pharmaceutically acceptable ester thereof.

19. The method of claim 18, wherein the androgenic agent is a testosterone ester.

20. The method of claim 19, wherein the testosterone ester is selected from the group consisting of testosterone enanthate, propionate, cypionate, phenylacetate, acetate, buciclate, heptanoate, decanoate, undecanoate, caprate and isocaprate.

21. The method of claim 20, wherein the testosterone ester is selected from the group consisting of testosterone enanthate, propionate and cypionate.

22. The method of claim 18, wherein the androgenic agent is testosterone.

23. The method of claim 16, wherein the progestin is selected from the group consisting of acetoxypregnenolone, allylestrenol, anagestone acetate, chlormadinone acetate, cyproterone, cyproterone acetate, desogestrel, dihydrogesterone, dimethisterone, ethisterone, ethynodiol diacetate, flurogestone acetate, gestadene, hydroxyprogesterone, hydroxyprogesterone acetate, hydroxyprogesterone caproate, hydroxymethylprogesterone, hydroxymethyl-progesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, and combinations thereof.

24. The method of claim 23, wherein the progestin is selected from the group consisting of progesterone, cyproterone acetate, norethindrone, norethindrone acetate and levonorgestrel.

25. The method of claim 16, wherein the polymeric carrier is selected from the group consisting of carbomers, hydrolyzed polyvinylalcohol, polyethylene oxide, polyacrylates, hydroxypropyl methylcellulose, hydroxypropyl cellulose, and combinations thereof.

26. The method of claim 25, wherein the carrier is polyethylene oxide or a carbomer.

27. The method of claim 15, wherein the dosage unit weighs in the range of approximately 10 mg to 15 mg.

28. The method of claim 16, wherein the androgenic agent and the progestin together represent approximately 40 wt. % to 85 wt. % of the buccal dosage unit.

29. The method of claim 28, wherein the androgenic agent and the progestin together represent approximately 50 wt. % to 85 wt. % of the buccal dosage unit.

30. A method for effecting contraception in a mammalian male individual, comprising buccally administering to the individual a pharmaceutical composition comprising an androgenic agent selected from the group consisting of testosterone and testosterone enanthate and a progestin selected from the group consisting of norethindrone and norethindrone acetate, using the buccal dosage of claim 15.

31. The method of claim 30, wherein the amount of androgenic agent administered is approximately 5 to 15 mg per day.

32. The dosage unit of claim 14, wherein the androgenic agent and the progestin together represent approximately 85 wt. % of the dosage unit.

33. The dosage unit of claim 12, wherein the androgenic agent represents approximately 50 wt. % of the unit and the progestin represents approximately 35 wt. % of the unit.

34. The dosage unit of claim 1, wherein the polymeric carrier erodes over an approximately twenty-four hour period.

35. The dosage unit of claim 1, wherein the polymeric carrier erodes over an approximately twelve hour period.

36. The method of claim 29, wherein the androgenic agent and the progestin together represent approximately 85 wt. % of the dosage unit.

37. The method of claim 27, wherein the androgenic agent represents approximately 50 wt. % of the unit and the progestin represents approximately 35 wt. % of the unit.

38. The method of claim 16, wherein the polymeric carrier erodes over an approximately twenty-four hour period.

39. The method of claim 16, wherein the polymeric carrier erodes over an approximately twelve hour period.

40. A buccal dosage unit for use in male contraception, comprising a compressed tablet of a polymeric carrier which adheres to the oral mucosa and erodes upon sustained contact therewith over a period of approximately eight to twenty-four hours, and, incorporated in the polymeric carrier, a contraceptive composition comprising approximately 50 wt. % testosterone and approximately 35 wt. % norethindrone, and wherein the weight of the tablet is in the range of approximately 5 mg to 20 mg.

* * * * *